US009110050B2

(12) United States Patent
Likuski et al.

(10) Patent No.: US 9,110,050 B2
(45) Date of Patent: Aug. 18, 2015

(54) MEASURING MULTI-ANALYTE SAMPLES USING AN IN-LINE FLOW CELL

(71) Applicant: Bio-Rad Laboratories, Inc., Hercules, CA (US)

(72) Inventors: Robert K. Likuski, Walnut Creek, CA (US); Anthony F. Prestigiacomo, Mill Valley, CA (US); Tong Le, Pinole, CA (US); Kurt D. Kramer, Pinole, CA (US); Donald J. Bartling, Novato, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/300,164

(22) Filed: Jun. 9, 2014

(65) Prior Publication Data

US 2015/0027207 A1    Jan. 29, 2015

Related U.S. Application Data

(62) Division of application No. 12/700,653, filed on Feb. 4, 2010, now Pat. No. 8,790,592.

(51) Int. Cl.
*B01L 3/00* (2006.01)
*G01N 33/49* (2006.01)
(Continued)

(52) U.S. Cl.
CPC .............. *G01N 33/4915* (2013.01); *G01N 1/28* (2013.01); *G01N 15/06* (2013.01); *G01N 21/6486* (2013.01); *G01N 30/06* (2013.01); *G01N 35/00* (2013.01); *G01N 35/1095* (2013.01); *G01N 35/1097* (2013.01); *G01N 2015/0693* (2013.01); *Y10T 436/2575* (2015.01)

(58) Field of Classification Search
CPC .............................. G01N 1/00; G01N 1220/00
USPC .................................. 422/500–504; 436/180
See application file for complete search history.

(56) References Cited

U.S. PATENT DOCUMENTS

| 4,586,190 A | 4/1986 | Tsuji |
| 5,299,141 A | 3/1994 | Hungerford et al. |

(Continued)

FOREIGN PATENT DOCUMENTS

| EP | 0275409 A2 | 7/1988 |
| EP | 1054250 A1 | 11/2000 |

(Continued)

OTHER PUBLICATIONS

International Search Report dated Apr. 20, 2011, from International Patent Application No. PCT/US11/23760 (3 pages).

(Continued)

*Primary Examiner* — Jyoti Nagpaul
(74) *Attorney, Agent, or Firm* — Kilpatrick Townsend & Stockton, LLP

(57) ABSTRACT

Methods and systems for analyzing ratios of analytes within a flowing sample are provided. The flowing sample can be processed in real-time to determine a time interval over which a predetermined amount of a group of analytes passes by a fixed point in a flow cell. The predetermined amount can be routed to a sample container for future processing. The sample can comprise diluted blood and the analytes can comprise a component of hemoglobin, such as A1c, and the total amount of hemoglobin, of which the predetermined amount is metered.

19 Claims, 10 Drawing Sheets

(51) Int. Cl.
*G01N 35/10* (2006.01)
*G01N 1/28* (2006.01)
*G01N 15/06* (2006.01)
*G01N 35/00* (2006.01)
*G01N 21/64* (2006.01)
*G01N 30/06* (2006.01)

(56) References Cited

U.S. PATENT DOCUMENTS

| | | | |
|---|---|---|---|
| 5,365,559 A | 11/1994 | Hsueh et al. | |
| 6,641,783 B1 | 11/2003 | Pidgeon et al. | |
| 7,318,900 B2 * | 1/2008 | DeMarco | 210/656 |
| 7,635,594 B2 | 12/2009 | Holmes et al. | |
| 2003/0103872 A1 | 6/2003 | Maier et al. | |
| 2006/0027490 A1 | 2/2006 | DeMarco | |
| 2007/0277596 A1 | 12/2007 | Kim et al. | |
| 2009/0103086 A1 | 4/2009 | Stark et al. | |

FOREIGN PATENT DOCUMENTS

| | | |
|---|---|---|
| JP | 2001-83165 A | 3/2001 |
| JP | 3941391 B | 7/2007 |
| JP | 2009-222398 A | 10/2009 |
| JP | 2010-008047 A | 1/2010 |
| WO | 2005/121780 A2 | 12/2005 |

OTHER PUBLICATIONS

Extended European Search Report mailed Jun. 3, 2014, from European Application No. 11740432.7 (10 pages).
Notice of Reasons for Rejection mailed Oct. 21, 2014, from Japanese Application No. 2012-552111 (10 pages).

* cited by examiner

MEASURING MULTI-ANALYTE SAMPLES USING AN IN-LINE FLOW CELL

CROSS-REFERENCE TO RELATED APPLICATIONS

The present patent application claims priority to U.S. patent application Ser. No. 12/700,653, entitled "MEASURING MULTI-ANALYTE SAMPLES USING AN IN-LINE FLOW CELL", filed on Feb. 4, 2010, which is hereby incorporated by reference.

BACKGROUND

The present invention generally relates to processing liquid samples containing an analyte, and more specifically to processing biological samples containing a biological analyte, with two or more components, using an in-line flow cell.

Blood tests, such as immunoassay or high performance liquid chromatography (HPLC), require analysis of the components of hemoglobin in a sample. Results of such tests can be expressed as a ratio of the amount of one component (e.g., hemoglobin A1c) of hemoglobin to the amount of a group of components (i.e., group amount). These ratios can be predictive of the presence and management of various diseases and physiological conditions, such as diabetes.

The group amount may differ from a total amount of components because of the exclusion of some components of hemoglobin, such as fetal hemoglobin and hemoglobin variants. The difference between the group amount and total amount is generally small, so as a first pass the total amount can be used as a good approximation for group the amount.

Problems with testing consistency can occur when the total response differs from sample to sample. Solutions have been proposed regarding this problem, as shown in co-assigned U.S. patent application Ser. No. 12/196,132. One current method is to maintain strict control of the total amount of hemoglobin by diluting a sample to a fixed concentration and then testing a fixed volume of the diluted sample, thereby providing a fixed total amount of hemoglobin.

Optimum results have not been achieved thus far, partially due to variability in the total/group amount of hemoglobin in an original sample, settling of the blood cells in the sample, and difficulties in accurately controlling the dilution ratio, as the dilution ratio will have a tolerance range. The first two contributors (i.e., variability and settling) result in sampled hemoglobin concentrations ranging from 90 to 360 grams/liter which give a normalized range of 1-4. Inaccuracies in controlling the dilution ratio can extend this range to 1-5. In a particular HPLC application, this 1-5 range corresponds to total chromatographic peak areas ranging from 1-5 AU-seconds, with a mid value of 3 AU-seconds. Quantification accuracy is compromised as this area deviates from the mid-value. At the extremes of the range, the sample may need to be re-run at a different dilution that results in an area closer to the mid-range. Accordingly, new methods for providing precise and reliable quantification of the components of hemoglobin, as well as other analytes, are desired.

BRIEF SUMMARY

Embodiments of the invention include a method for measuring analytes in a sample. A sample containing analytes may be flowed through a detector. A measurand of the analytes passing through the detector may be measured. A time interval over which the measurand reaches a predetermined quantity may be determined. A portion of the flowing sample containing the predetermined quantity of the measurand may be diverted to a sample volume.

Embodiments of the invention also include a system for processing a sample. The system includes a flow cell having an entrance and an exit. A pump system may be fluidly coupled to the entrance of the flow cell. The pump system may be configured to move the sample through the flow cell. A detector may be functionally attached to the flow cell. A first transition valve may be fluidly coupled to the exit of the flow cell. A controller may be configured to determine when a fixed amount of a group of components of hemoglobin has flowed through the light beam based on a signal from the detector. The controller may be configured to switch the first transition valve in order to route the portion of the sample containing the fixed amount of the components of hemoglobin.

Other embodiments of the invention are directed to systems and computer readable media associated with methods described herein.

A better understanding of the nature and advantages of the present invention may be gained with reference to the following detailed description and the accompanying drawings.

DETAILED DESCRIPTION

Figure 1A:
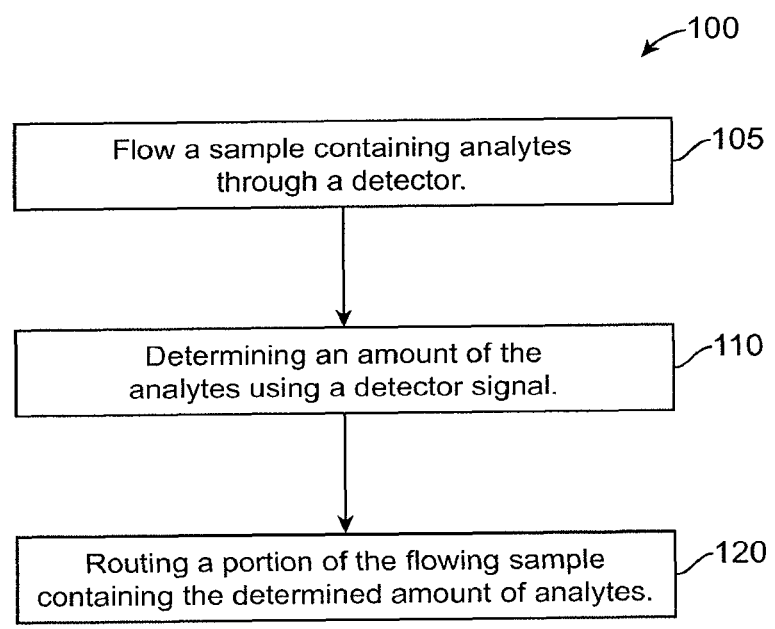
FIG. 1A is a flow diagram of a method for measuring analyte samples, according to an embodiment of the invention.

Embodiments of the invention provide methods and systems for analyzing samples containing analytes. An initial course dilution can take place, where the sample is diluted to a desired amount. The sample may then be flowed through an inline flow cell where the absorbance of the diluted sample is measured. The absorbance is related, preferably linearly, to the concentration of a group of analytes within the sample. The absorbance may be measured by passing a transverse beam of light through the diluted sample and detecting how much of the beam of light has been absorbed by the analytes within the sample. A fixed amount of the analytes passing through the beam of light can be determined by a real-time calculation of the absorbance values. The calculation may be integration of the varying absorbance values with respect to a start time and an end time.

The start time may be defined shortly after the diluted sample is detected passing through the beam of light, and the end time may be calculated for when a desired amount of the analytes will pass through the beam of light. Suitable valves may be configured to divert a sample plug between the start and end times to an HPLC injection loop, or to a reaction chamber for an immunoassay. The injection loop may be partially filled, rather than overfilled as customary with the prior art. The system may be calibrated by adjusting an integral threshold for the final value, and accordingly the end time for the integration, so that a desired HPLC group response can be achieved. Accordingly, each sample run can calibrate a subsequent sample run to improve the response accuracy.

It should be appreciated that the fixed amount of the analytes flowing through a light beam need not be associated with a fixed mass but rather the sum of the responses of the group of components. In a HPLC system, a response is typically the area of a chromatographic peak. The relationship between the fixed amount and the sum of the selected responses can be viewed as a calibration.

The fixed amount of sample is further processed to determine the response to a specific analyte, which is the numerator response and the response to a group of analytes, which is the denominator response. The ratio of the numerator response to the denominator response is the desired response ratio. This response ratio can be refined by further calibration and used for predicting various diseases when the analytes are components of hemoglobin. Controlling the denominator response value to a desired and fixed amount can provide more consistent and useful testing results. The numerator analyte may represent an amount of a modified form of hemoglobin, including A1c, labile A1c, and carbamylated A1c. The numerator analyte may also represent an amount of a variant form of hemoglobin, including E, D, S, and C variants. The denominator response represents the sum of the responses of a group of components of hemoglobin. That group may include all of the components of hemoglobin or it may exclude some components such as the hemoglobin variants. For testing of hemoglobin from adults, it may also exclude any components identified as fetal hemoglobin. This further processing is done by an analytical technique, including HPLC or immuno-assay. In some embodiments, HPLC or immuno-assay may be used to determine only the numerator response with the value of the integral threshold being used as the denominator response. The response ratio can be controlled to a higher degree than with prior art methods by tighter control of the response range of the denominator analyte, which can result in improved ratio consistency and test results.

Knowing an exact amount of a component of hemoglobin in a diluted blood sample is helpful for various tests, such as a measurement of A1c using immunoassay or HPLC. It is also beneficial to be able to consistently provide the same mass of hemoglobin in successive tests. Accordingly, embodiments of the invention provide a fixed or known amount of hemoglobin to a sample volume (e.g., a sample container such as an injection loop) for later testing. It should be appreciated that other embodiments of the invention can be directed towards measuring samples other than blood and analytes other than hemoglobin, such as other biological samples (e.g., urine) or non-biological samples.

I. Exemplary Method and System:

FIG. 1A is a flowchart illustrating a method 100 for analyzing samples containing analytes according to an embodiment of the present invention. At step 105, a sample is flowed through a detector. The sample is generally a liquid sample including a plurality of one or more types of analytes. As used herein, an analyte is any substance within a greater sample which is the subject of analysis. In some embodiments, the sample is a diluted blood sample, and the analytes are components of hemoglobin. The detector can be a flow cell which detects certain types of analytes based on light-absorption values; for example, light at 415 nm may be used for detecting hemoglobin. Accordingly, the detector can be used to aid in measuring a fixed amount of a component of hemoglobin. In some embodiments, the flow cell outputs a signal to a chromatography analyzer. As used herein, "signal" can comprise a single signal or a plurality of signals. The signal may be a voltage, a current, or a digital value.

In step 110, an amount of an analyte in the flowing sample of hemoglobin passing by a fixed location, e.g., the center of the light beam, in the flow cell is determined over a time interval using the detector signal. The determination is based on integrating real-time light-absorption values of the detector signal. As the values are calculated in real-time, the amount of mass of the analyte, which passes by the fixed location of the detector, can be determined as a function of time. In some embodiments, a mass calculation can be based on a real-time integration of the product of concentration and flow-rate over time. In another embodiment, this integral can be adequately approximated by summation of absorbance values measured at fixed time intervals. In some embodiments, when the integral or summation reaches a predetermined threshold, a fixed amount of hemoglobin has passed the fixed point in the detector. In some embodiments, the mass will not be calculated (e.g., integrated) until an amount of a measurand of the analytes is detected to pass a threshold. In some embodiments, the concentration of analytes may non-predicatively vary due to flow rate changes; thus in some embodiments, the mass will not be calculated until a stabilized concentration of analytes is detected. As used herein, a measurand is as aspect of an analyte which can be measured. For example, in some embodiments a measurand can be absorbance units (AU) derived from an electrical signal (e.g., voltage, current), and/or the electrical signal alone.

In some embodiments, the flow area (as distinguished from chromatographic area) can be limited to prevent overfilling of the volume of a sample container. In another embodiment, the flow area is a calibration of a previous flow area from a previous analysis of the sample to achieve a desired test response. For example, a flow sample may result in a chromatograph response of 4 (AU-sec) when a target value of 3 was desired. Accordingly, the flow area used for the first sample can be proportionately reduced and applied to a second sample to achieve the desired response. This refinement may be repeated until the desired response is achieved. In another embodiment, pluralities of different analytes masses are calculated, such as the total amount of hemoglobin rather than just one specific type of hemoglobin.

Assuming a constant flow rate and a constant concentration value, the following equation may be used to determine mass of the analyte over the time interval T, where F=flow rate (vol/time) and c=concentration (mass/vol):

$$m = FcT$$

The absorptivity of the analyte may have a linear relationship with the concentration value. Thus, concentration may be replaced with the following equation, where a=absorptivity, and b=path length (distance traveled by light through the flow cell):

$$c = \frac{AU}{ab} \text{ thus, } m = F\frac{AU}{ab}T$$

In some embodiments, a variable concentration can be expressed in terms of a varying absorbance value AU by the following equation:

$$c(t) = \frac{1}{ab} AU(t)$$

Assuming a constant flow rate and a varying concentration value over time, the following integral may be used to determine the mass of the analyte:

$$m = \frac{F}{ab} \int_{t_0}^{t_0+T} AU(t)dt$$

Assuming a variable flow rate and a variable concentration value over time, the following integral may be used to determine the mass of the analyte:

$$m = \frac{1}{ab} \int_{t_0}^{t_0+T} F(t)AU(t)dt$$

In step 120, the portion of the sample containing the fixed amount is routed to a sample volume for later testing. The portion of the sample can be diverted without stopping the flow of the sample. For example, at the beginning of the time interval, the portion of the sample is initially diverted to a sample container; and at the end of the time interval, the sample can be rerouted back to its original flow output. In some embodiments, this diversion and rerouting is performed by switching valves at various times based on the time interval. The portion of the sample contains the known amount of mass of the analyte and can be routed for further tests, such as HPLC or an immunoassay test. Accordingly, the use of method 100 does not require controlling the sample concentration to an exact value, but rather works according to a given mass of the sample. This results in improved consistency between samples testing, as concentration differences between the samples do not affect the ability to provide a fixed amount of analyte.

Figure 1B:
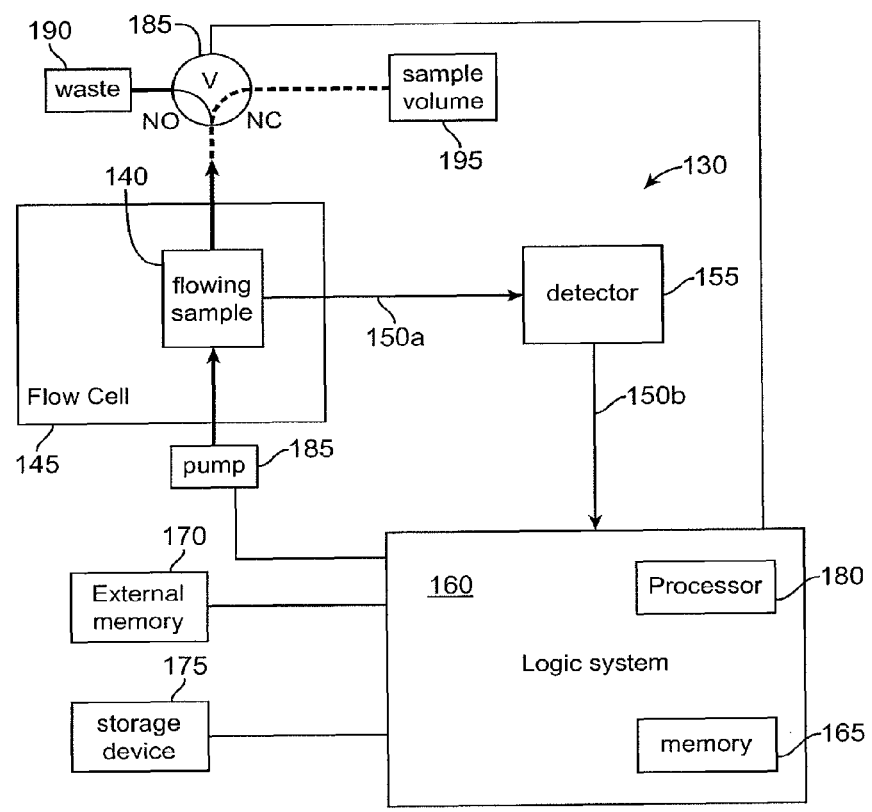
FIG. 1B is a schematic diagram of a system for measuring analyte samples, according to an embodiment of the invention.

FIG. 1B illustrates a system 130 according to an embodiment of the present invention. As shown, system 130 includes a flowing sample 140, such as diluted blood, flowing within a flow cell 145. A physical characteristic 150a, (i.e., a measurand) such as a sample absorbance or fluorescence intensity value, from the sample is detected by detector 155. A signal 150b is sent from detector 155 to logic system 160 that functions as a controller. The signal 150b is proportionally based on the amount of physical characteristic 150a. The data from signal 150b may be stored in a local memory 165 or an external memory 170 or a storage device 175. In some embodiments, an analog to digital converter converts an analog signal to digital form. The sample flows through the flow cell by operation of pump 185. The sample is routed through the flow cell 145 and to a solenoid operated 3-way transition valve 185. The 3-way transition valve 185 has a normally open pathway NO and a normally closed NC pathway. The normally open pathway NO fluidly connects the waste volume 190 to the flow cell 145, when the 3-way valve is not activated (i.e., no power to the solenoid) during a waste filling configuration. When the away valve is activated during a sample filling configuration, the normally open NO pathway is closed, and the normally closed NC pathway is opened to fluidly connect the sample volume 195 to the flow cell 145.

The logic system 160 may be, or may include, a computer system, ASIC, microprocessor, etc. It may also include or be coupled with a display (e.g., monitor, LED display, etc.) and a user input device (e.g., mouse, keyboard, buttons, etc.). The logic system 160 can be configured to perform analysis on the flowing sample 140 in a real-time manner, as described with respect to method 100. The logic system 160 and the other components may be part of a stand-alone or network connected computer system, or they may be directly attached to or incorporated in a separate testing device, such as an HPLC or immunoassay testing device. The logic system 160 may also include analysis software that executes in a processor 180.

In use, the flowing sample 140 can be flowed through the flow cell 145 by actuating pump 185, the pump 185 being controlled by logic system 160. As the flowing sample 140 passes through the flow cell 145, the detector 155 generates a signal 150b from the physical characteristic 150a of an analyte in the flowing sample 140. The logic system 160 uses the signal 150b to determine the amount of analyte passing through the flow cell over time. The logic system 160 switches the 3-way valve 185 to route a portion of the flowing sample 145 to the sample volume 195, which provides the sample volume 195 with a fixed amount of analyte. After the sample volume 195 has been provided with the fixed amount of analyte, the pump 185 can cease operation to halt the flowing sample 140 and/or deactivate the 3-way valve 185 to route the flowing sample 140 back to waste 190. The portion of sample within the test volume 195 can then be submitted to further tests.

Figure 2:
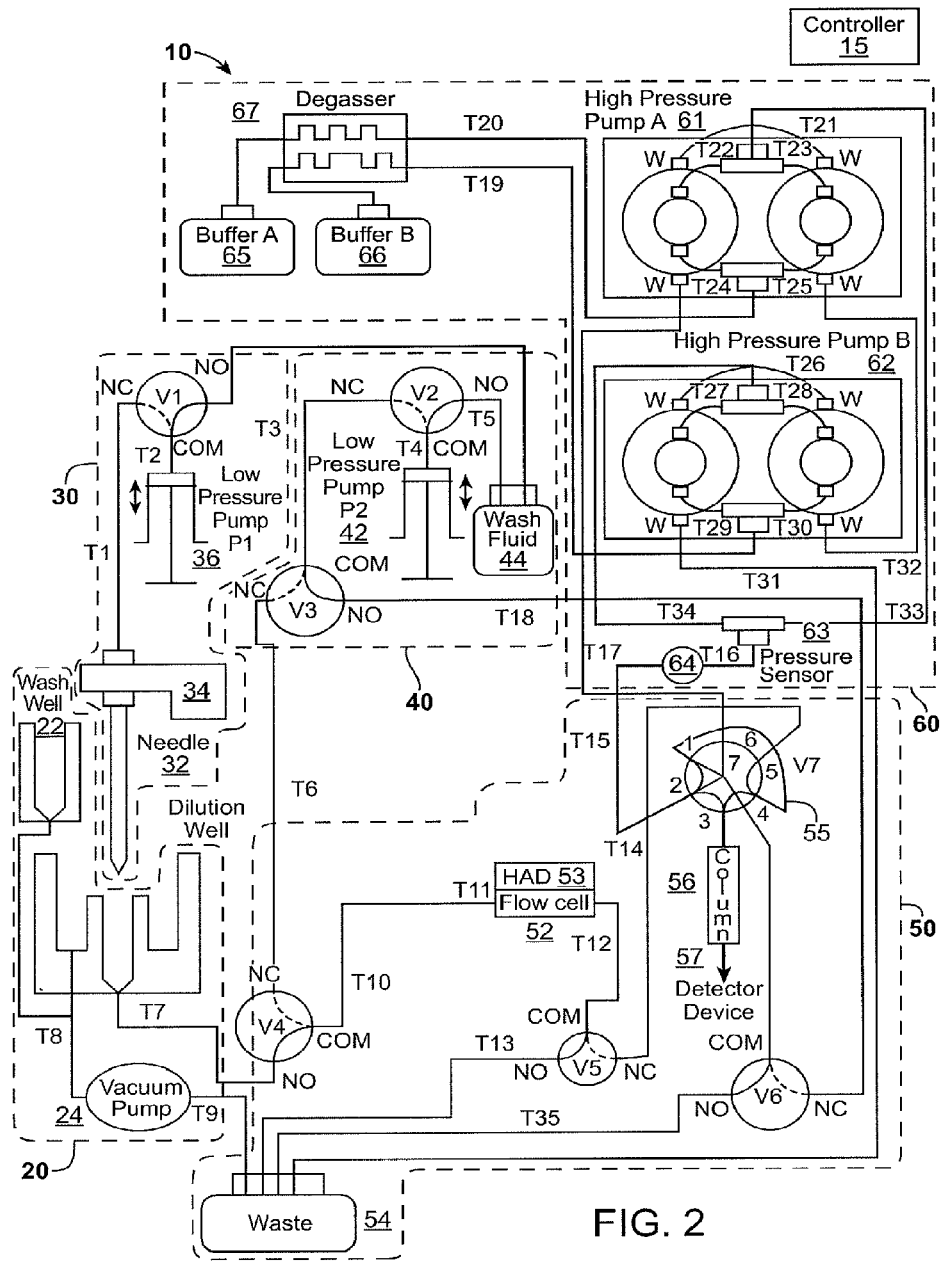
FIG. 2 is a schematic diagram of a system for measuring analyte samples, according to an embodiment of the invention.
Figure 3A:
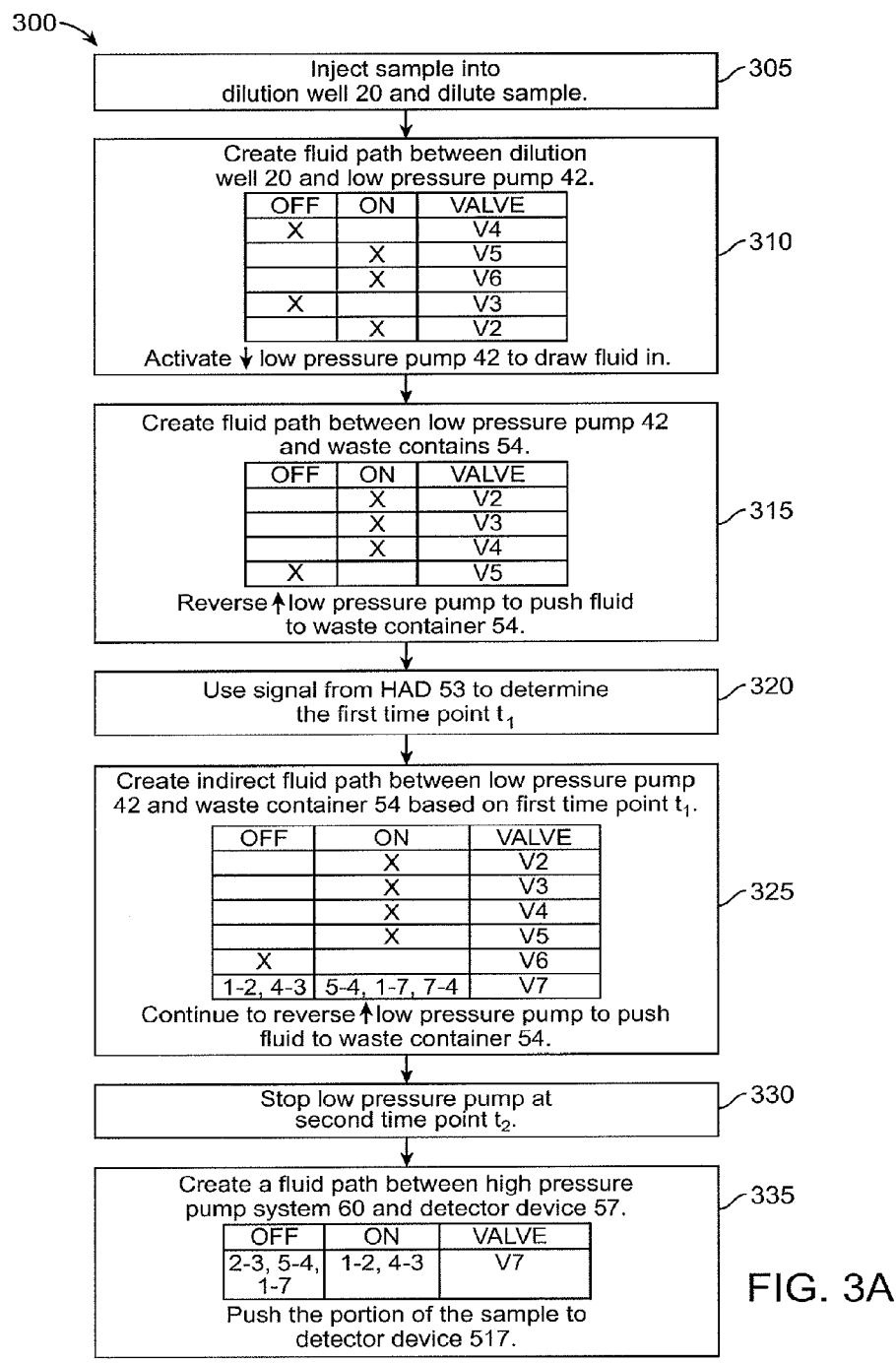
FIG. 3A is a flow diagram of a method for measuring analyte samples, according to an embodiment of the invention.

II. Exemplary Valve System:

FIG. 2 shows a diagram of a system 10 for measuring analyte samples, in a non-operational mode. FIGS. 3B-3E show the system 10 in use according to the method of FIG. 3A. In some embodiments, the methods 100 and 300 can be performed using system 10, although the invention is not limited as such.

With reference to FIG. 2, the system 10 includes a controller 15 which controls all operational aspects (e.g., valves, sensors, pumps, detectors) of the system 10. The controller 15 is generally configured similarly to the logic system 130, as described with reference to FIG. 1B. The controller 15 may also comprise a plurality of sub-controllers. The controller 15 can be a mixture of hardware and software, such as a general purpose computer, purpose-built computer, or remote server. In some embodiments, the controller 15 is part of a separate test system which is fluidly coupled to system 10, such as an HPLC device or an immunoassay test device.

A. Dilution Well:

The system 10 includes a dilution well 20. The dilution well 20 can hold a dilution liquid for diluting samples. The controller 15 can be configured to dilute and mix samples in the dilution well 20. Portions T8 and T9 of the dilution well 20 can be fluidly connected to a wash well 22 for washing the needle and a pump 24 for driving wash fluid.

B. Needle System:

A needle system 30 is moveably connected to the dilution well 20. A needle 32 is connected to moveable needle arm 34. The needle arm 34 can be manually or robotically configured by the controller 15 to move the needle 32 from a sample container (not shown) to the dilution well 20. A line T1 can fluidly connect the needle 32 to a normally closed NC connection of transition valve V1, which is generally a solenoid operated 3-way valve. A low pressure pump 36, which is generally a syringe-style pump, can be connected to the common COM connection of the transition valve V1. The NO connection is connected to a container containing wash fluid, which also serves as dilution fluid.

C. Pump System:

A pump system 40 includes a low pressure pump 42, which is generally a syringe-style pump. The low pressure pump 42 is fluidly connected to a common line COM of a transition valve V2, which is generally a solenoid operated 3-way valve. A normally closed NC connection of transition valve V2 is fluidly connected to the common connection COM of transition valve V3, which is generally a solenoid operated 3-way valve. A normally open NO connection of transition valve V2 is fluidly connected to a wash fluid container 44, which contains a wash fluid. The wash fluid container 44 can also be fluidly connected to the normally open NO connection of transition valve V1 of the needle system 30.

D. Flow Cell System:

A flow cell system 50 is fluidly connected to the dilution well 20 and pump system 40. An output line T7 of the dilution well 20 is also fluidly connected to a normally open NO connection of transition valve V4, which is generally a solenoid operated 3-way valve. In an alternate embodiment, V4 is a 4-way valve.

An output line T6 of the pump system 40 is fluidly connected to a normally closed NC connection of transition valve V4 via normally closed NC connection of transition valve V3, which is generally a solenoid operated 3-way valve. A common COM connection of transition valve V4 is fluidly connected to output line T10. The output line T10 is fluidly connected to an input connection of flow cell 52.

The flow cell 52 includes a window pane which is operatively attached to hemoglobin absorption detector (HAD) 53. The HAD 53 generally includes a photodiode and a light source, such as a 415 nm LED. In other embodiments, different types of analyte detectors are used. The photodiode can generate an electrical signal (e.g., voltage or current) when light of a certain frequency is received. The HAD is electrically connected to controller 15 to supply the signal to controller 15. The controller 15 is configured to determine an amount of analyte passing through the flow cell 52 by analyzing the signal.

An output connection of flow cell 52 is fluidly connected to line T12, which is fluidly connected to a common COM connection of transition valve V5, which can be a solenoid operated 3-way valve. An output line T13 is fluidly connected between a normally open NO connection of transition valve V5 and waste container 54. Fluid line T9 of the dilution well is also fluidly connected to waste container 54. Fluid line T14 is fluidly connected between a normally closed connection NC of transition valve V5 and a sample container 55.

The sample container 55 is configured as a loop with a predetermined volume fluidly connected to injection valve V7. Injection valve V7 is a multi-solenoid valve with connections 1, 2, 3, 4, 5, 6, and 7. Fluid transmission is possible between connections 1-2, 1-7, 2-3, 2-7, 3-4, 4-5, 4-7, and 6-7 depending on solenoid actuation. The sample container is physically connected to connections 1 and 4 and can be fluidly connected to connections 2-3-7 of injection valve V7. Connection 3 of injection valve V7 is fluidly connected to a separation column 56, which is fluidly connected to a detector device 57. Connection 7 of the injection valve V7 is fluidly connected to the common COM connection of transition valve V6. Fluid line T35 is fluidly connected between a normally open NO connection of transition valve V6, which is generally a solenoid operated 3-way valve, and waste container 54. Fluid line T18 is fluidly connected between a normally closed NC connection of transition valve V6 and a normally open connection of transition valve V3 of the pump system 40.

E. High Pressure Pump System:

The sample container 55 in valve V7 is alternately fluidly connected to the low pressure flow cell system 50 and the high pressure pump system 60. The high pressure pump system 60 includes high pressure pump 61 and high pressure pump 62. Fluid lines T33 and T34 fluidly connect the pumps 61 and 62, respectively, to a T-junction 63. Fluid line T16 is fluidly connected between T-junction 63 and a pressure sensor 64. Fluid line T15 is fluidly connected between pressure sensor 64 and connection 2 of injection valve V7 of the flow cell system 50. Fluid line T17 is fluidly connected between connection 6 of injection valve V7 and the entrance piston wash port, W, of high pressure pump 61. The seven remaining wash ports W are either internally connected or connected by external tubing to the exit wash port, which connects to tubing T31. The other end of T31 connects to the waste container 54. Buffer containers 65 and 66 are fluidly connected to degasser 67. Fluid line T20 is fluidly connected between degasser 66 and high pressure pump 61. Fluid line T19 is fluidly connected between degasser 66 and high pressure pump 62.

Figure 3B:
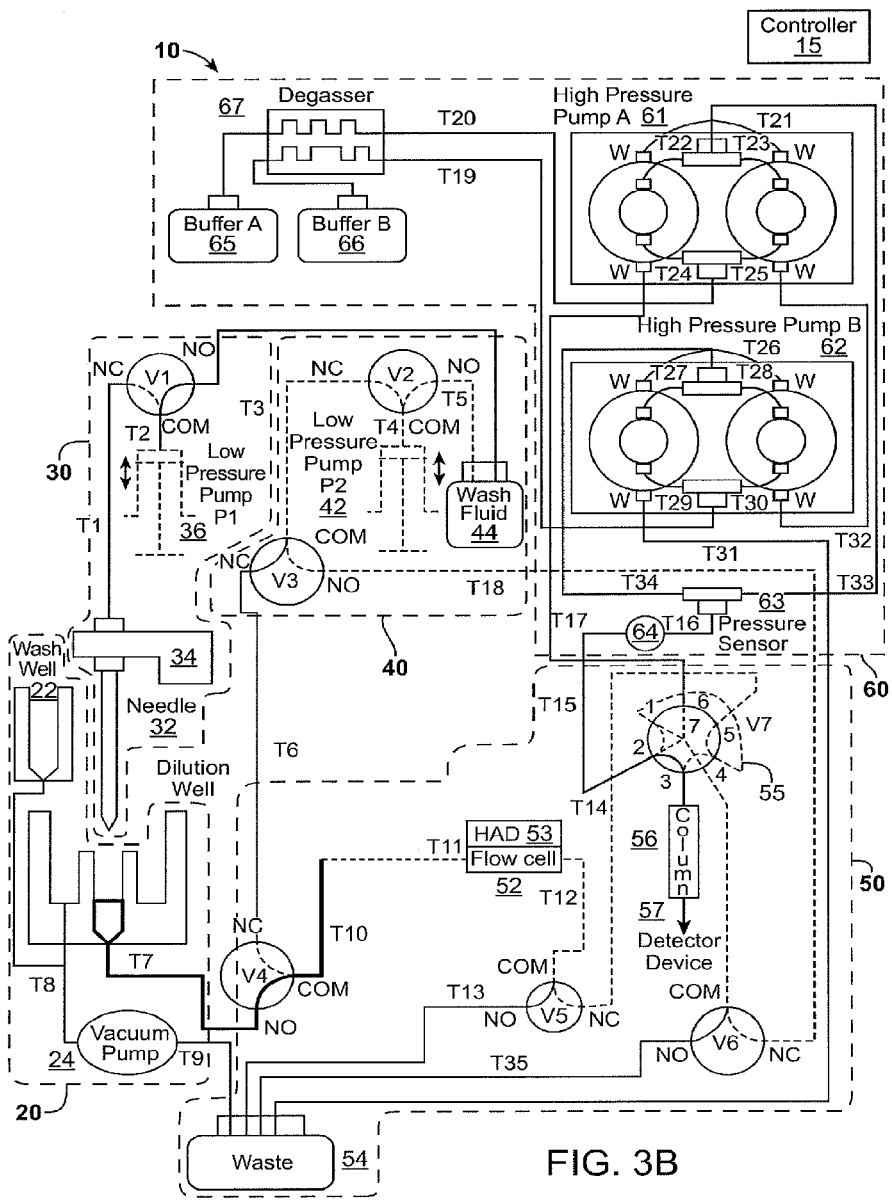
FIGS. 3B-3E are schematic diagrams of the system of FIG. 2 in various states of use, according to embodiments of the invention.

III. Exemplary Valve System in Use:

With reference to FIGS. 3A-3E, system 10 can be used as shown by the method 300. In step 305, system 10 is controlled by the controller 15 to move the needle arm 34 and retrieve a sample, as shown by FIG. 3B. The needle arm 34 retrieves the sample, and is moved to the dilution well 20 to inject the sample into the dilution well 20 using needle 32. The sample is then diluted in the dilution well 20 by dispensing additional dilution (same as wash) fluid after the sample. The sample path is shown by the heavy dark line and a dotted line, the dotted portion representing wash fluid which previously primed and cleaned the fluid path.

In step 310, the system 10 is controlled by the controller 15 to create a fluid path between dilution well 20 and low pressure pump 42 as further shown by FIG. 3B. Accordingly, transition valve V4 is not activated to remain normally open; transition valve V5 is activated to close the normally open NO connection and open the normally closed NC connection; transition valve V6 is activated to close the normally open NO connection and open the normally closed NC connection; injection valve V7 is opened between connections 5-4, 1-7, and 7-4; transition valve V6 is activated to close the normally open NO connection and open the normally closed NC connection; transition valve V3 is not activated to remain normally open NO; transition valve V2 is activated to close the normally open NO connection and open the normally closed NC connection; and low pressure pump 42 is activated to draw fluid within. As shown, the sample is momentarily halted at a point between the transition valve V4 and the flow cell 52 by stopping pump 42.

Figure 3C:
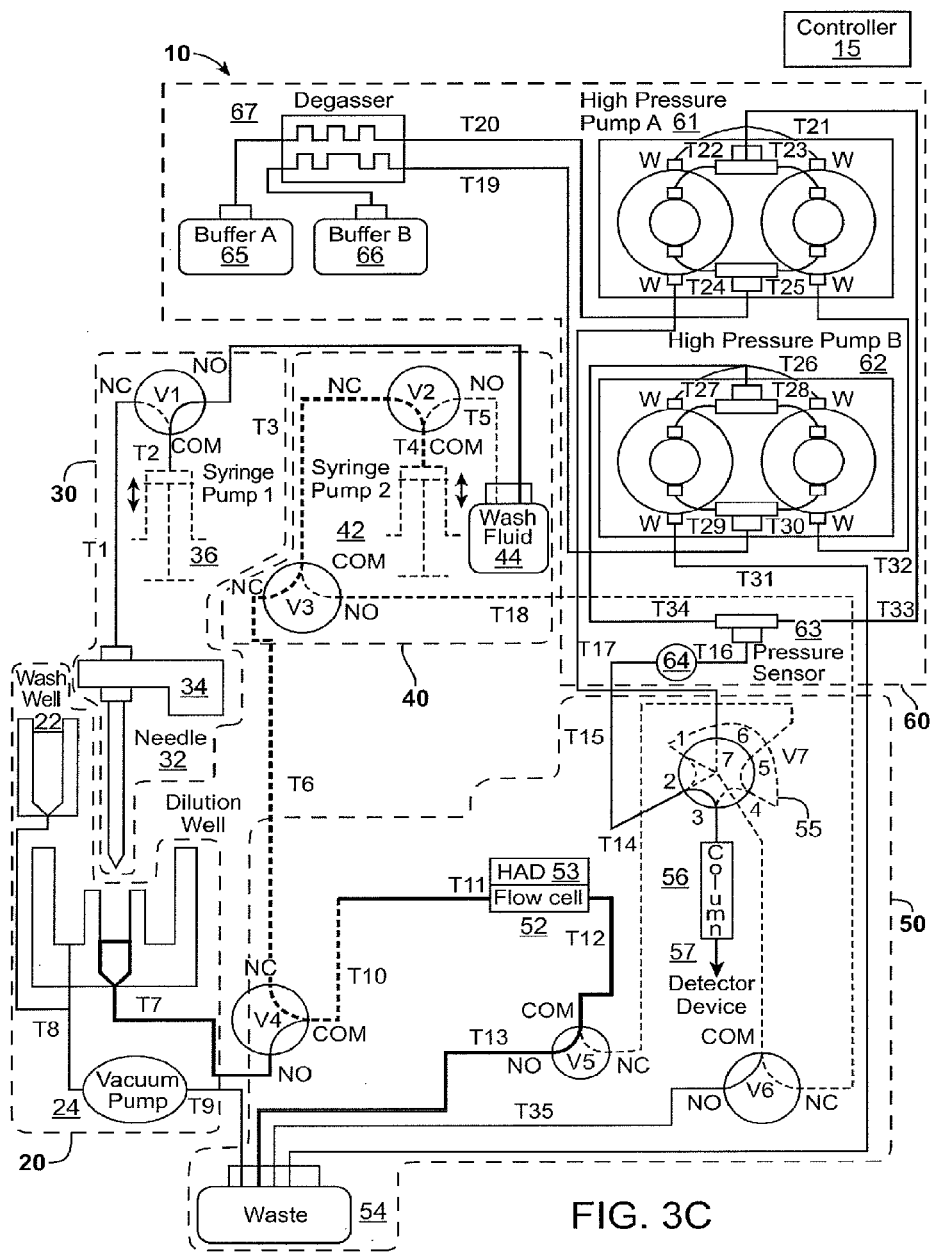

In step 315, system 10 passes the sample through the flow cell system 50, as shown in FIG. 3C. In step 315, the system 10 is controlled by the controller 15 to create a direct fluid path between low pressure pump 42 and waste container 54. Accordingly, transition valve V2 remains activated to open the normally closed NC connection; transition valve V3 is activated to close the normally open NO connection and open the normally closed NC connection; transition valve V4 is activated to close the normally open NO connection and open the normally closed NC connection; transition valve V5 is deactivated to open the normally open NO connection; and the low pressure pump 42 is reversed to push fluid out and force the sample to waste container 54.

In step 320, the HAD 53 generates an electrical signal when the sample flows through the flow cell 52. The controller 15 can convert electrical signal into a measurand that is linearly proportional to the concentration of the measured analytes. The analytes may be one or more types of hemoglobin, such as hemoglobin A1c. The measurand may be a quantity of absorbance units (AU). The controller 15 may be configured to detect when the measurand reaches a first threshold, which can be a minimum quantity of the measurand. Once the first threshold value is reached, the controller 15 can determine a first time point $t_1$ of a time interval over which the measurand is integrated to provide the desired mass of the analyte. The first time point $t_1$ provides the basis to control transition valves V5 and V6. The controller 15 can determine a second time point $t_2$ which is the end of the time interval. The second time point $t_2$ can be chosen to provide a desired mass of analyte for a later test. The second time point $t_2$ can be calibrated by adjusting (i.e., increasing or decreasing) a second threshold from a previous test sample to provide or come closer to a desired mass.

Figure 3D:
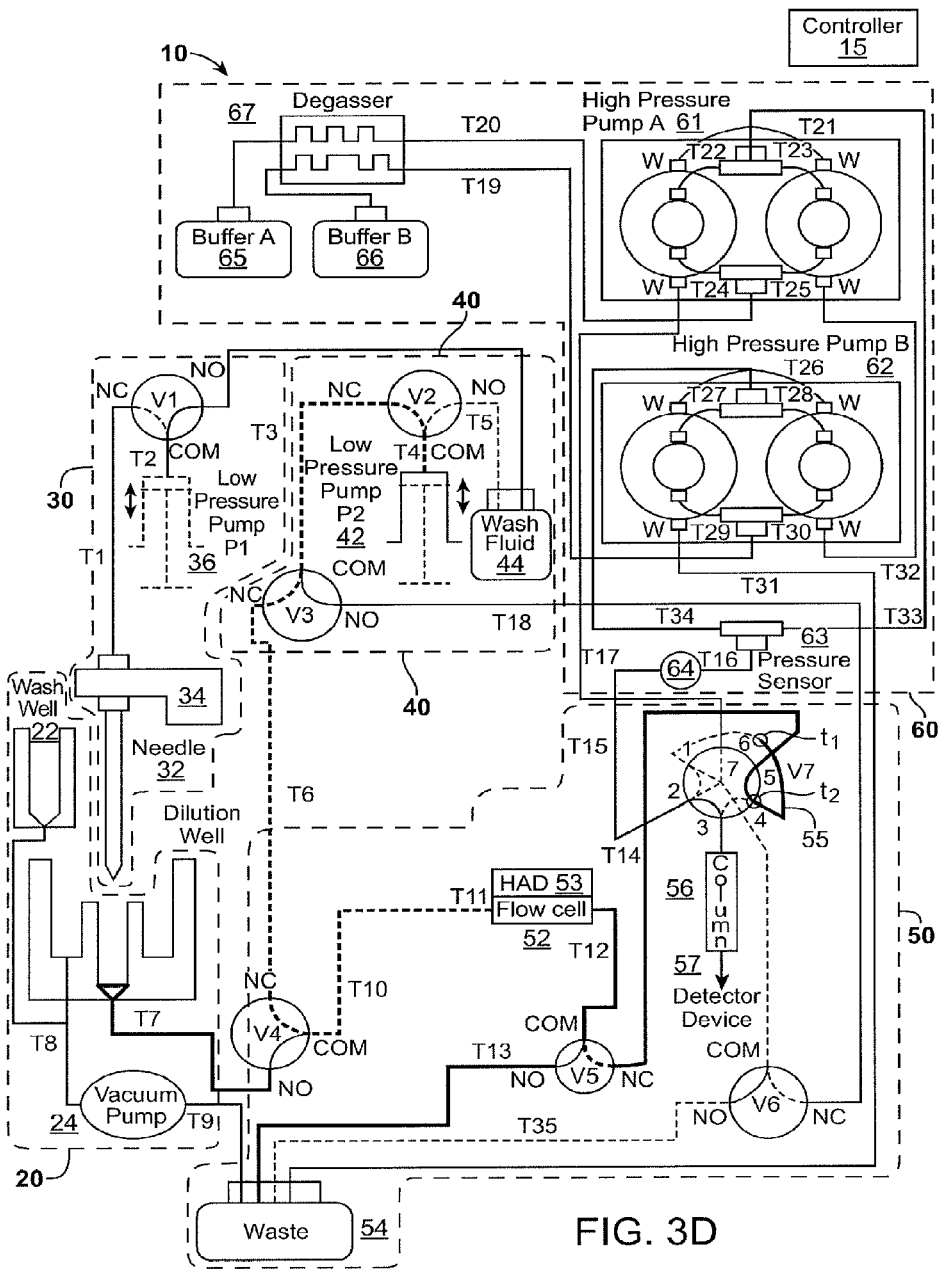

In step 325, system 10 additionally passes a portion of the sample to the sample container 55, as shown in FIG. 3D. The system 10 is controlled by the controller 15 to create an indirect fluid path between low pressure pump 42 and waste container 54, based on the first time point $t_1$. Accordingly, transition valves V2, V3, and V4 remain activated to open the normally closed NC connections; transition valve V5 is activated to close the normally open NO connection and open the normally closed NC connection; injection valve V7 is opened only between connections 5-4, 1-7, and 7-4; transition valve V6 is not activated to remain normally open NO; and low pressure pump 42 continues to push fluid out and force the sample into container 55.

In step 330, the controller halts the low pressure pump 42 based on a timer interval from the first time point $t_1$ to the second time point $t_2$. Accordingly, a portion of the sample having a predetermined mass of an analyte (i.e., the sample plug) is contained within the sample container 55. The controller 15 can be configured to position the sample plug such that an end of the sample plug corresponding to the second time point $t_2$ is placed at connection 4 of injection valve V7. Connection 4 of injection valve V7 may be disconnected from connection 5 and connected to connection 3 at the end of the sample plug corresponding to the second time point $t_2$.

The first time point $t_1$ and the second time point $t_2$ are used for a real-time summation or integration of a measurand (e.g., absorbance values) detected by the HAD 53 to provide a fixed mass of an analyte. The first time point $t_1$ can be based on a first threshold amount of the measurand detected by the HAD 53. The second time point $t_1$ can be based on a second threshold amount of the measurand detected by the HAD 53. The second time point $t_2$ can be chosen to provide a desired amount of mass for a later test. Thus, the second time point $t_2$ can be determined to prevent the mass introduced onto column 55 from exceeding the desired mass. The second time point $t_2$ may also be constrained to prevent overflow and/or complete filling of the sample container 55. A sample plug is shown in the sample container 55 between the portions of the sample corresponding to the first time point $t_1$ and the second time point $t_2$. The sample plug contains the fixed mass of the analyte used for later testing, which was determined from an integration of a measurand between the first time point $t_1$ and the second time point $t_2$. Alternatively, the fixed mass between the first and second time point can be used directly in the analytical calculation without further measurement.

Figure 3E:
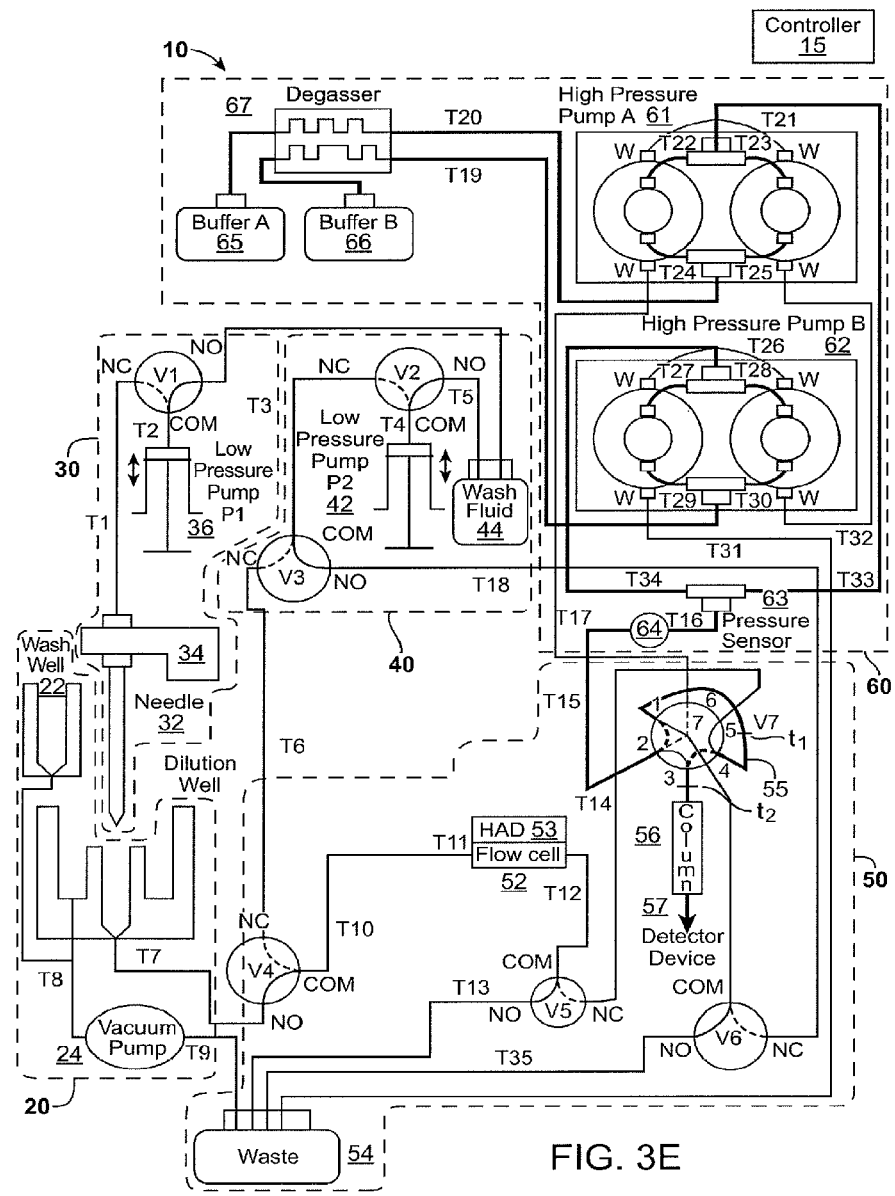

In step 335, system 10 additionally passes the sample plug through column 56 to a detector device 57, as shown in FIG. 3E. The system 10 is controlled by the controller 15 to create a direct fluid path between high pressure pump system 60 and detector device 57. Accordingly, the injection valve V7 is activated to close connections 2-3, 5-4, and 1-7, and open connections 1-2, 4-3. Buffer solutions from buffer containers 65 and 66 are degassed by degasser 67 and forced through the high pressure pump system 60 to push the portion of the sample to the column 56 and the detector device 57 for testing. The detector device 57 can be a HPLC device, or a test device for immunoassay. The sample plug corresponding to the first time point $t_1$ and the second time point $t_2$, and containing the fixed amount of analyte is shown moving towards the detector device 57 for testing. In HPLC, the column 56 serves to separate the sample into its component parts.

In an alternative embodiment, an average concentration of an analyte can be determined to provide a fixed amount of the analyte. The sample is first passed through the flow cell 52 to overfill the sample container 55 at a rapid flow rate. Accordingly, the volume of the sample container 55 would be completely full between connections 1 and 4 of the injection valve V7. In this embodiment, the flow cell 52 may be directly connected to the injection valve V7, and thus the valve V5 is not necessary.

The signal from the HAD 53 is used to calculate the concentration of an analyte which passed through the flow cell 52, and thus to determine the average concentration of the analyte within the overfilled sample container 55. For this determination, only the delay time between the HAD-53 and connection 4 of V7 need be determined. As the volume of the sample container 55 is known and fixed, the total amount of the analyte within the sample container can be calculated from the average concentration. Based on these calculations, controller 15 can the control the high pressure pump system 60 and the injection valve V7 to inject a portion of the contents of sample container 55. The injection takes place over a time interval which provides the column 56 and detector device 57 with a portion of the sample containing the fixed and desired amount of the analyte.

The time interval is determined from the average concentration value of the analyte, sample volume, injection flow rate of the high pressure pump system 60, and the required amount of analyte. At the beginning of the time interval the injection valve V7 closes connections 2-3, 5-4, and 1-7, and open connections 1-2, 4-3, and the high pressure pump system 60 injects a portion of the sample container 55 into the column 56 (i.e., the injecting position). At the end of the time interval the injection valve V7 reverts to close connections 2-3, 5-4, and 1-7, and open connections 1-2, 4-3 (i.e., the loading position) to prevent further injection into the column 56.

The injection valve V7 may be configured to have a fast response time. For example at a flow rate of 50 µl/sec, (3 ml/min) a 5 µl injection from a 20 µl sample container 55 would require the valve V7 to be in the injecting position for 100 msec. This embodiment may help to eliminate intermixing of the sample with wash solution at the sample boundaries and reduce positioning issues during the transfer of a sample to the injection valve V7, simplify the calculation for the fixed amount of analyte, eliminate valve V5, and allow for rapid overfilling of the sample container 55 at a higher flow rate.

It should be appreciated that the system 10 can perform various other methods supplemental to analyte analysis, in accordance with operation of the various valves and pumps, such as back-flushing and cleaning operations.

Figure 4B:
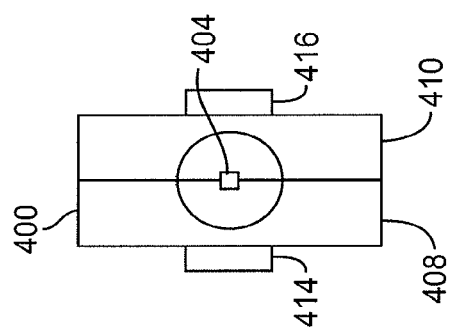
FIGS. 4A and 4B show a cross-sectional and end views, respectively, of a flow cell, according to an embodiment of the invention.
Figure 4A:
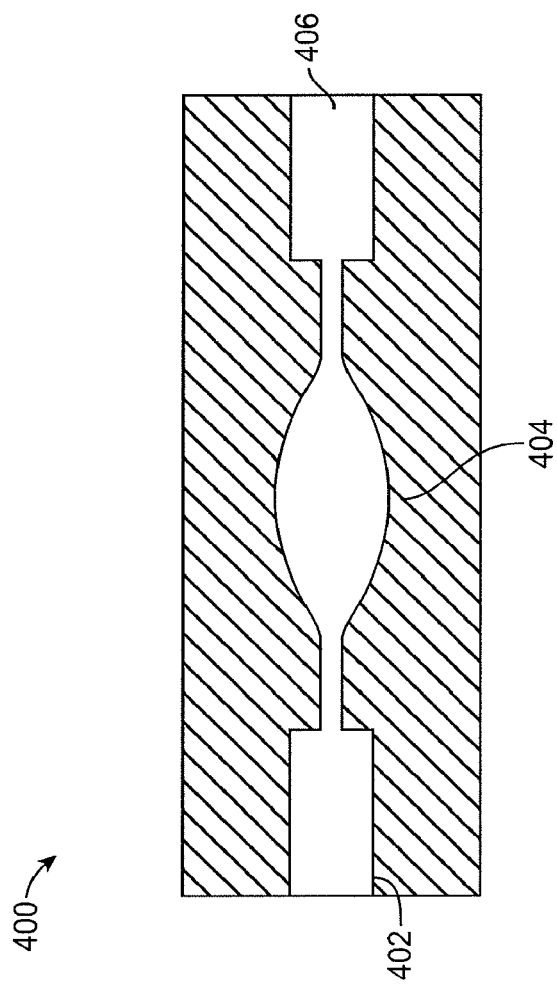

IV. Exemplary Flow Cell:

FIGS. 4A and 4B show views of a flow cell 400 according to an embodiment of the present invention. The flow cell 400 can be used with an analyte detector for use with the systems and methods disclosed herein, such as flow cell 52. The flow cell 400 includes an entry section 402, an analysis section 404, and an exit section 406, through all of which a liquid sample is flowed. The analysis section 404 can be an expanded section as shown. In some embodiments, the transitions between the sections are configured to provide laminar flow at the expected flow rate of the system. This can thus prevent turbulence in the flow, which can result in inconsistent test results. In some embodiments, the analysis section 404 is a straight channel with a square cross-section measuring 0.03×0.03 inches.

The flow cell 400 can be constructed from sections 408 and 410 which are constructed from an optically polished and transparent material, such as glass or a transparent polymer, which may be UV transparent Polymethylmethacrylate (PMMA) in some embodiments. The transparent material can allow light at 415 nm to pass through. A light transmitter 414 is placed on section 408 for transmitting light transversely across the analysis section 404 to a receiver 416 placed on section 410. In some embodiments, the light transmitter 414 transmits light from a 415 nm LED through a pin-hole aperture, and the receiver 416 is a photodiode for detecting absorbance intensity. It should be appreciated that other optical sources at different wavelengths can be used to detect the presence of other analytes. The light transmitter 414 and receiver 416 generally include suitable electrical wiring for connecting to a signal processing device. The length of the light path through the measured fluid is chosen as a best balance for good signal to noise and good linearity.

In use, a fluid sample is flowed into the entry section 402 and fully envelops the area of the analysis section 404, and exits the exit section 406. Light from the light transmitter 414 is transmitted at a certain frequency to the receiver 416 in a direction transverse to the flow of the sample. Analytes present in the sample will absorb a portion of the transmitted light, thus preventing 100% transmittal to the receiver 416. The amount of light detected by the receiver 416 is converted into an electrical signal, which can be a voltage or a current. The receiver 416 continuously outputs the signal to an analysis device, which can determine analyte information based on the signal values. The analysis device can be, for example, the controller 15 or logic system 160 as described herein, which can calculate analyte concentration and amount.

V. Exemplary Chromatogram

Figure 5:
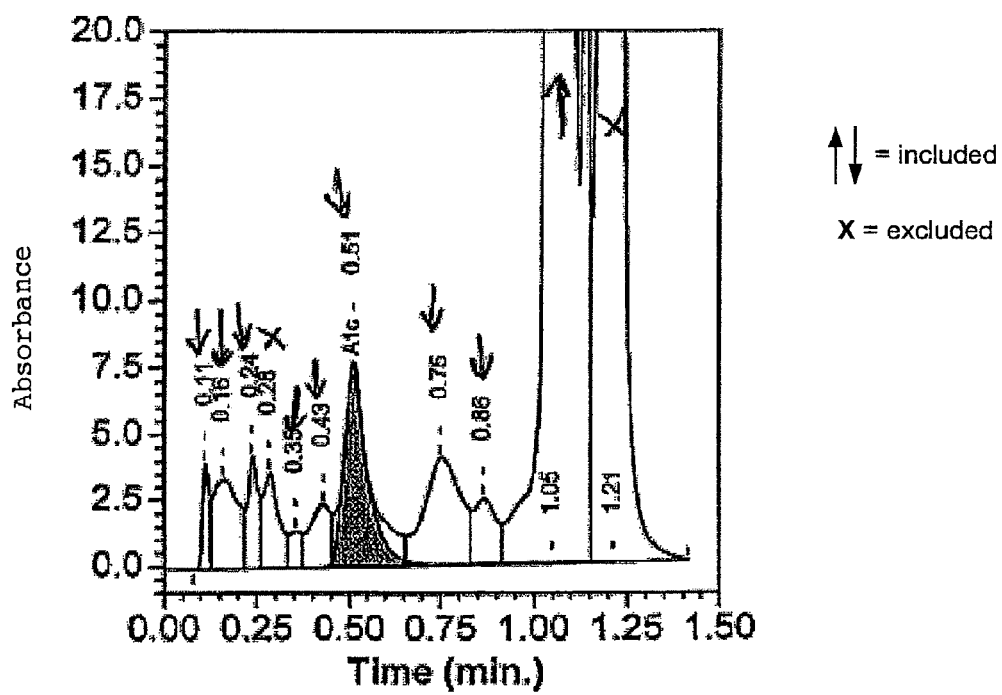
FIG. 5 shows an exemplary chromatogram of a diluted blood sample, according to an embodiment of the invention.

FIG. 5 shows a chromatogram 500 of a diluted blood sample according to an embodiment of the invention. The peaks in chromatogram 500 correspond to the values in the following chart.

| Peak Name | Calibrated Area % | Area % | Retention Time (Min) | Peak Area |
|---|---|---|---|---|
| Unknown | — | 0.6 | 0.111 | 9603 |
| A1a | — | 1.5 | 0.159 | 25090 |
| A1b | — | 0.9 | 0.235 | 15333 |
| F | — | 1.0 | 0.282 | 17356 |
| Unknown | — | 0.3 | 0.353 | 5171 |
| LA1c | — | 1.0 | 0.427 | 16869 |
| A1c | 7.3 | — | .510 | 56351 |
| P3 | — | 2.9 | 0.750 | 48614 |
| P4 | — | 1.0 | 0.863 | 16474 |
| Ao | — | 51.9 | 1.046 | 858844 |
| C | — | 35.3 | 1.212 | 584833 |
| | | | | Total = 1,654,537 |

The chromatogram 500 shows a small F (fetal hemoglobin) peak and a large C variant peak that are excluded from the group area. These peaks are not separated when passed through the HAD 53. The absorbance measured by the HAD 53 is the sum of the absorbance values of all of the peaks shown (i.e., total response). A threshold is set so as to control the sum to a desired value, which here is a total area of 1,654,537 (arbitrary units). To obtain the group areas for the denominator response value (i.e., group amount), the F area and the C area are subtracted from the total area, as shown by the "X" marks. Thus the denominator response value is thus 1,052,348, or 1 (i.e., 1,654,537−(584833+17356)=1,052,348). Embodiments of the invention provide the ability to control and calibrate the total area, to accordingly control the denominator response value.

A clinically significant quantity is determined from the chromatogram 500. The group amount will undesirably vary over the 1-5 range according to prior art methods, which embodiments of the invention address. The accuracy to which the clinically significant quantity can be determined becomes poorer as the group amount moves away from a desired mid-range value, at which calibration is performed to move the group closer to the desired mid-range value. A prior-art process referred to as "correction" may be performed in addition to calibration to handle group amounts that are not at mid-range, but this process is not adequate at the limits of the range. According to the prior art, the sample is re-analyzed with a different dilution so that the group amount will be close to mid-range. However, re-analyzing is undesirable especially if the special dilution is performed manually.

The specific details of the specific aspects of the present invention may be combined in any suitable manner without departing from the spirit and scope of embodiments of the invention. However, other embodiments of the invention may be directed to specific embodiments relating to each individual aspects, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission. Suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g., a hard drive or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. For example, in an alternative embodiment, the detector is configured to detect metallic analytes of a biological or non-biological sample based on detected electromagnetic field values. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method for measuring analytes in a sample, the method comprising:
   flowing a sample containing analytes through a detector;
   measuring a measurand of the analytes passing through the detector;
   determining a time interval over which the measurand reaches a predetermined quantity of mass, wherein measuring the measurand comprises performing a real-time integration of the measurand over the time interval;
   forming a sample plug based on the time interval over which the measurand reaches the predetermined quantity of mass; and
   diverting a portion of the flowing sample containing the sample plug to a sample volume.

2. The method of claim 1, wherein the measurand has a linear relationship with analyte concentration.

3. The method of claim 2, wherein the measurand is based on light absorbance of analyte.

4. The method of claim 1, wherein the time interval is pre-determined.

5. The method of claim 1, wherein the time interval starts at a first time point that is determined by a first measured threshold of the measurand.

6. The method of claim 5, wherein the sample is flowed into a waste output before the first time point.

7. The method of claim 6, wherein the first time point is the basis to switch at least one valve for diverting the portion of the flowing sample from the waste output to the sample volume.

8. The method of claim 1, wherein the time interval ends at a second time point that is determined by a second measured threshold of the measurand.

9. The method of claim 8, wherein the second threshold is determined by a calibration of a second threshold from a previous sample such that the second threshold is at or closer to a desired value.

10. The method of claim 1, wherein the sample comprises a blood dilution.

11. The method of claim 10, wherein the analyte of the blood dilution is a type of hemoglobin.

12. The method of claim 11, wherein the type of hemoglobin is one of A1c, labile A1c, carbamylated A1c, E, D, S, or C.

13. The method of claim 1, wherein measuring a measurand of the analytes passing through the detector comprises determining an average amount of the analytes passing through the detector over the time interval to completely fill the sample volume.

14. The method of claim 13, further comprising:
   determining a total amount of the analytes within the sample container from the average concentration.

15. The method of claim 13, further comprising:
   injecting a portion of the sample container containing a desired amount of the analytes to a detector device.

16. The method of claim 1, further comprising controlling the flowing sample to flow at a low pressure through the detector.

17. The method of claim 1, wherein the predetermined quantity of mass is based on a fixed mass of hemoglobin.

18. The method of claim 1, wherein the sample volume is a part of the injector of an HPLC system.

19. The method of claim 1, wherein the sample volume is a part of a reaction chamber for an immune-assay system.

* * * * *